US005776201A

United States Patent [19]
Colleran et al.

[11] Patent Number: 5,776,201
[45] Date of Patent: Jul. 7, 1998

[54] MODULAR FEMORAL TRIAL SYSTEM

[75] Inventors: Dennis P. Colleran, Plainville; Robert S. Brown, Boston; David G. Sheehan, Carver, all of Mass.

[73] Assignee: Johnson & Johnson Professional, Inc., Raynham, Mass.

[21] Appl. No.: 537,023

[22] Filed: Oct. 2, 1995

[51] Int. Cl.⁶ ....................................................... A61F 2/38
[52] U.S. Cl. ............................................. 623/20; 606/88
[58] Field of Search .............................. 606/87, 88, 102, 606/53, 60; 623/20

[56] References Cited

U.S. PATENT DOCUMENTS 4,721,104  1/1988  Kaufman et al. ............................ 606/88
5,181,925  1/1993  Houston et al. ............................. 623/20
5,258,032  11/1993  Bertin ........................................ 623/20

FOREIGN PATENT DOCUMENTS 9014806  12/1990  WIPO ....................................... 623/20

OTHER PUBLICATIONS

Richards Mfg. Co., 1982. pp. 30,31, and 34.

Primary Examiner—Michael Buiz
Assistant Examiner—Julian W. Woo
Attorney, Agent, or Firm—Susan M. Schmitt

[57] ABSTRACT

A modular femoral trial system is provided having femoral trial bases of various sizes and adapters which may be used to convert the base from a cruciate retaining trial to a cruciate sacrificing trial or a trial for an implant with increased built in stability.

5 Claims, 4 Drawing Sheets

MODULAR FEMORAL TRIAL SYSTEM

FIELD OF THE INVENTION

The present invention relates to a modular femoral trial system used during knee replacement surgery to size the femoral portion of the prothesis to be implanted.

BACKGROUND OF THE INVENTION

Femoral trials are used in knee replacement surgery to assist the surgeon in determining the appropriate size and type of implant to use on a particular patient. Typically in such procedures a femoral trial is placed on a prepared femoral surface and a tibial trial is placed on the prepared tibial surface. Various adjustments may be made to the cuts on either the femoral or tibial surfaces and different femoral and tibial trial sizes are considered for use. The knee is flexed and extended to determine whether the component fit and placement is appropriate or not. If not, various other sizes of femoral and tibial trials are used until the best fit is determined. Typically, the femoral trials used in such procedures form a group or system including all or most of the possible sizes to be used.

Although most physicians begin surgery with a general understanding of what type of knee replacement will be done, i.e., a cruciate ligament retaining knee replacement system, a cruciate ligament sacrificing system, or TC3 (revision knee system). Some situations require the surgeon to change the planned implant type during a surgical procedure. In presently existing systems each type of surgery will require a separate sterilized tray with every size implant used for that type of surgery. For example, cruciate retaining surgical procedures have a total of ten possible femoral knee trials, five right side femoral trials and five left side femoral trials. Cruciate substituting femoral trial trays contain five left side femoral trials and five right side femoral trials. TC3 surgical procedures use a femoral trial tray with four left side femoral trials and four right side femoral trials. Thus, to accommodate the possibility of each type of surgery three trays must be available with a total of twenty-eight femoral trials.

SUMMARY OF THE INVENTION

The present invention provides a modular femoral trial system which reduces the total number of trays and the number of units necessary to prepare for a possibility of cruciate retaining, cruciate sacrificing or TC3 knee replacement operations. The system of a preferred embodiment comprises five left side femoral trials and five right side femoral trials with five adaptable removable center pieces for adapting the femoral trials to a cruciate sacrificing type femoral implant, and four adapters for changing the femoral trials to a TC3 type knee replacement trial. The femoral trials are presented on a single sterilization tray as opposed to three different sterilization trays for each of the three types of knee replacement surgery. In the preferred embodiment, each modular trial system for a given femoral trial size, comprises two base femoral components (one left and one right) and two box or adaptor components (one for stabilized and one for TC3). These four components can be assembled to create any femoral trial type for either the left or right side for a given femoral trial size. The modular trials are very easy to assemble, thus providing a simplified system that may be used during an operative knee replacement procedure.

DETAILED DESCRIPTION OF THE DRAWINGS

DETAILED DESCRIPTION OF THE PREFERRED EMBODIMENT

Figure 1:
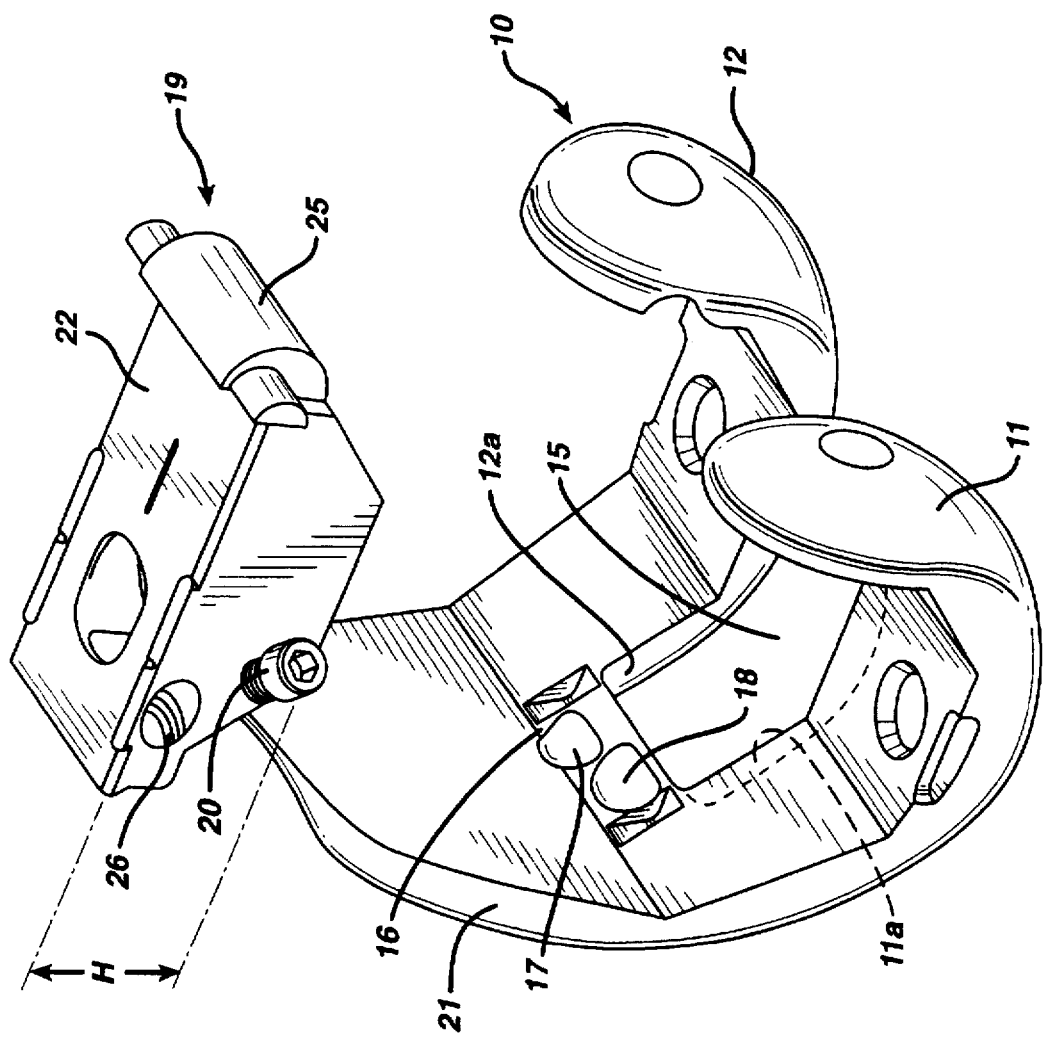
FIG. 1 is an exploded perspective view of a femoral trial with an inserted adapter.
Figure 2:
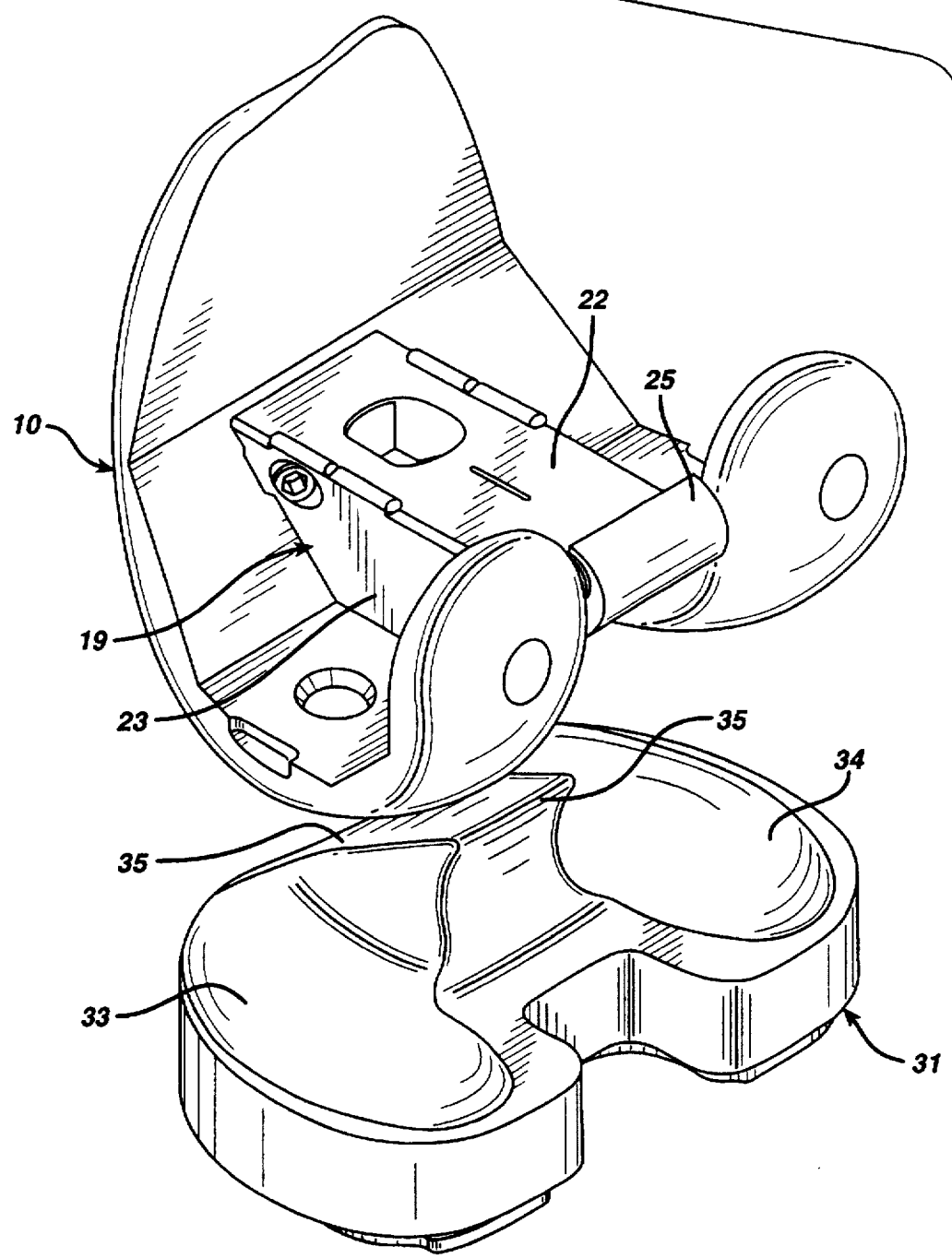
FIG. 2 is an exploded perspective view of a femoral and tibial trial system including the femoral trial and inserted adaptor of the present invention.
Figure 3:
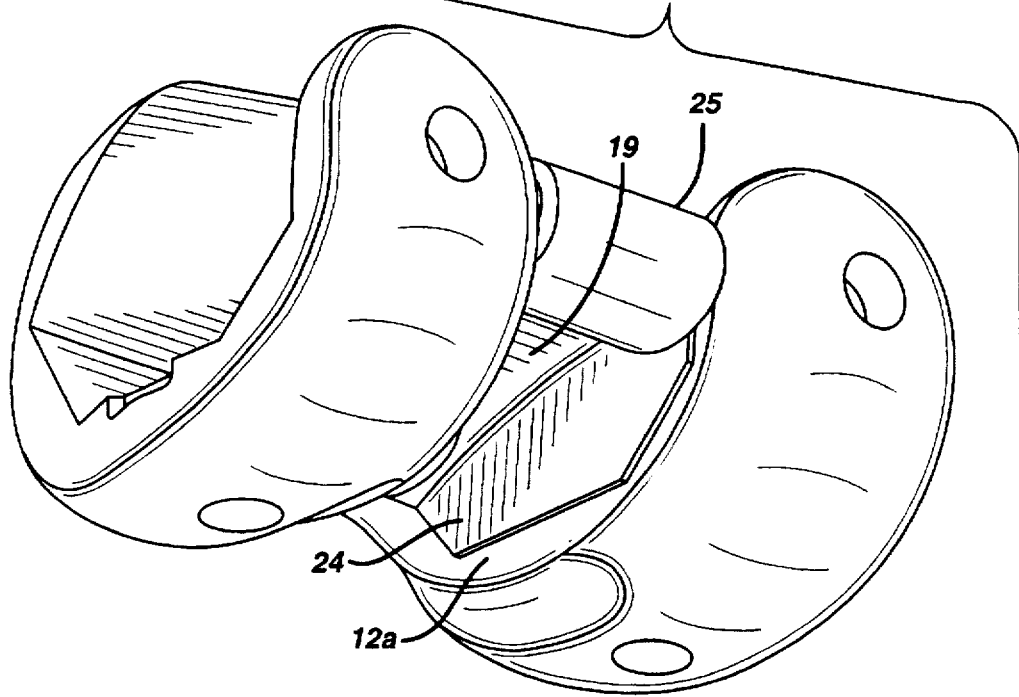
FIG. 3 is an exploded bottom perspective view of a femoral and tibial trial system including the femoral trial and inserted adaptor of the present invention.
Figure 3:
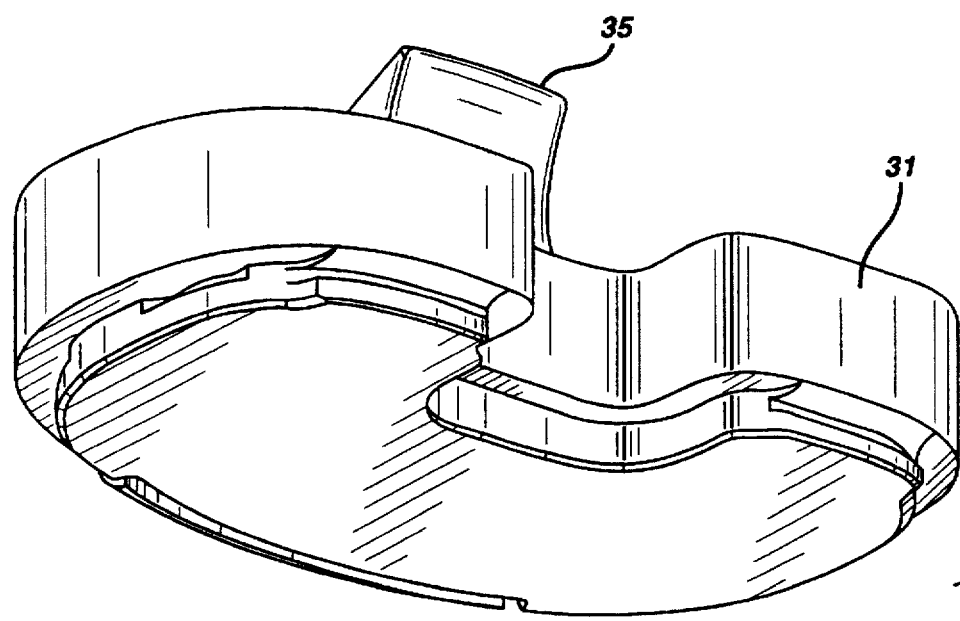

Referring now to FIGS. 1–3 a femoral trial base component 10 is illustrated comprising a medial condyle portion 11 and a lateral condyle portion 12. Inner walls 11a, 12a of the condyle portions 11, 12, respectively, define an opening 15 between the condyle portions 11, 12. The condyle portions 11, 12 are joined to the anterior side 21 by a flange 16. The flange 16 includes a plurality of centrally located cavities 17 and 18 for receiving screw 20 located on adaptor 19.

The adaptor 19 comprises a base 22 having side walls 23, 24 extending down from the base 22, and a cam member 25 situated on the posterior side of the base 22. The adaptor 19 is sized so that side walls 23, 24 extend partially within the opening 15 and flush against inner walls 11a, 12a respectively. The adaptor 19 further comprises a threaded screw 20 and a threaded hole 26. The screw 20 is arranged to fix the adaptor 19 to the femoral base 10.

FIGS. 2 and 3 illustrate a tibial trial component 31 adjacent the femoral trial base 10. The adaptor 19 is affixed to the base 10. The base 10 is thereby converted to a femoral trial for a cruciate sacrificing or revision knee implant. The height of the adaptor, (H), will vary depending upon whether a cruciate sacrificing or a TC3 (revision) artificial knee will be implanted.

The tibial trial 31 comprises a base 32 having a medial condyle surface 33 and a lateral condyle surface 34 arranged to engage and support condyle portions 11, 12 of femoral base 10, respectively. The tibial trial 31 further comprises a tibial spine 35. The tibial spine 35 extends into opening 15 of femoral base 10 and is surrounded by side walls 23, 24, cam 25, and base 22 of adaptor 19.

The adaptor 19 forms a box which engages with the tibial spine 35 to stabilize or constrain the knee movement in a cruciate sacrificing knee replacement surgery. The cam 25 engages with the tibial spine 35 when the knee is flexed to prevent hyperflexion and the side walls 23, 24 engage with the spine 35 to prevent excessive lateral movement of the tibial and femoral components, 31, 10 with respect to each other. In a cruciate retaining procedure the ligaments remain intact and thus the tibial spine 35 and adaptor 19 are not used as trial components.

Figure 4:
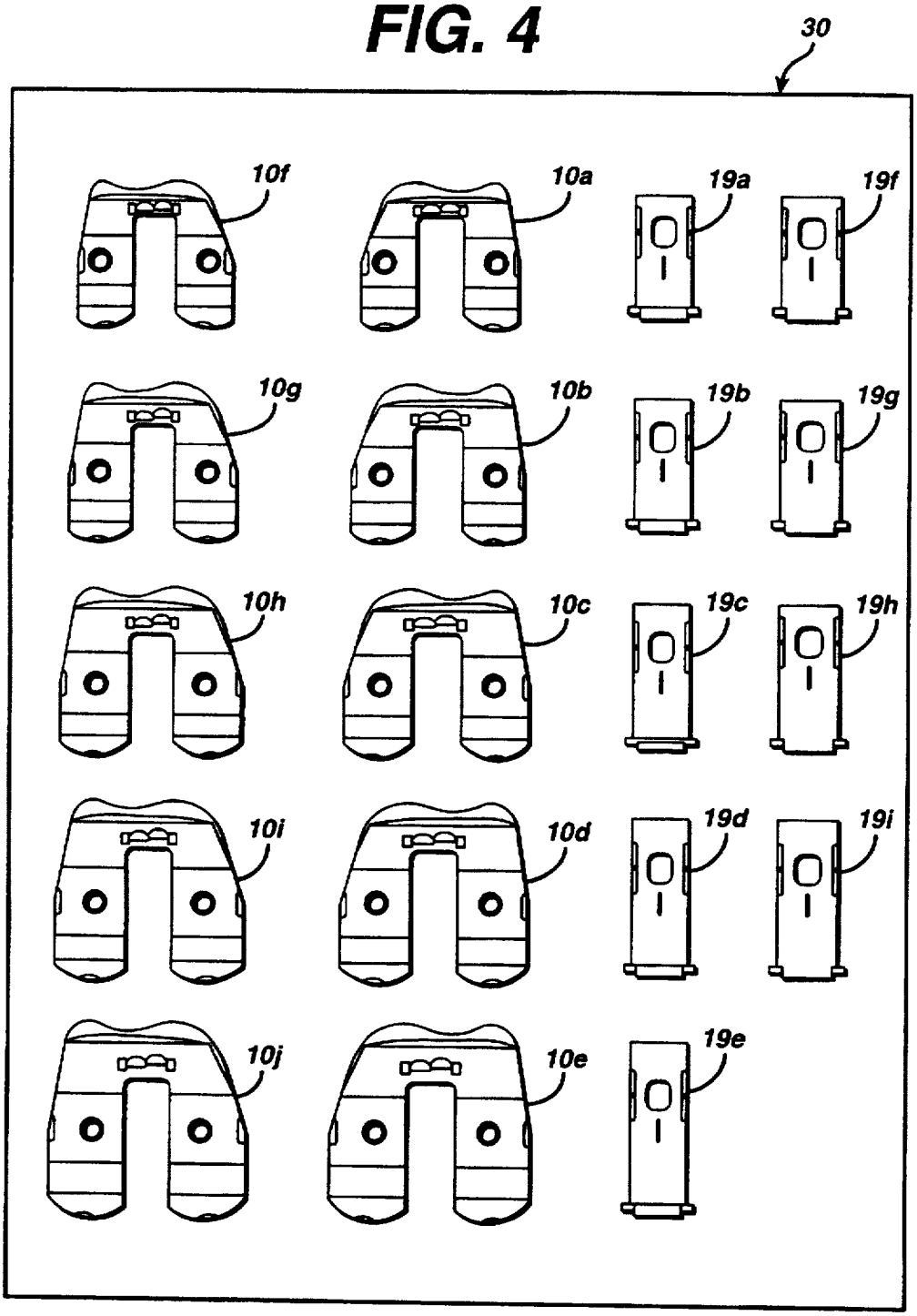
FIG. 4 is a top plan view of a femoral trial system of the present invention in the form of a sterilization tray.

FIG. 4 illustrates femoral sterilization tray 30 containing the modules of the femoral trial system. The tray includes five different sized right side femorals trials 10a–10e and five different sized left side femoral trials 10f–10j; five cruciate sacrificing adapters 19a–19e; and four TC3 adapters 19f–19i. Trials 10a and 10f, corresponding to a femoral implant size having an A/P length of 2.178 in., may be used with adapters 19a or 19f. Trials 10b and 10g, corresponding to a femoral implant size having an A/P length of 2.426 in., may be used with adapters 19b or 19g. Trials 10c and 10h, corresponding to a femoral implant size having an A/P length of 2.564 in., may be used with adapters 19c or 19h. Trials 10d and 10i, corresponding to a femoral implant size having an A/P length of 2.741 in., may be used with adapters 19d or 19i. Trials 10e and 10j, corresponding to a femoral implant size having an A/P length of 2.956 in., may be used with adaptor 19e.

A trial is typically made of cobalt chrome or stainless steel. They are preferably stainless steel. The screw 20 threaded. The adaptor screw 20 may be used to attach any adaptor to any femoral trial base. The system is preferably packaged in a single tray 30 modular components, 10f–10i, and 19a–19i, are sterilized on the tray and are sterile packaged for use in a sterilized operating room. Sterilization tray is preferably formed of stainless steel or plastic. The adapters 19a–19i are typically formed of stainless steel.

Although the present invention is described with reference to a particular preferred embodiment, numerous equivalents or modifications may be made without departing from the spirit and scope of the invention. The specific embodiment described herein is not intended to limit the claimed invention.

We claim:

1. A modular femoral trial kit for use in surgical procedures for implanting a femoral prosthesis comprising:
    a femoral base portion including medical and lateral condyle portions said condyle portions forming a groove therebetween;
    a plurality of removable attachable knee joint stabilizing adapters, each of said plurality of adapters comprising a base having a pair of side walls extending from said base and a fixation device, each of said plurality of adapters arranged to be removably attached with said fixation device to said femoral base portion to provide a knee joint stabilizing trial device wherein said side walls are fixable in a position adjacent said groove, wherein each of said plurality of adapters has a different stabilizing capacity.

2. A modular femoral trial kit for use in surgical procedures for implanting femoral prosthesis comprising:
    a plurality of femoral trial base portions each of said base portions comprising medial and lateral condyle portions, said condyle portions forming a groove therebetween; and
    a plurality of removable attachable knee joint stabilizing adapters, each of said plurality adapters comprising a base having a pair of side walls extending from said base, a cam, and a fixation device, each of said plurality of adapters arranged to be removably attached with said fixation device to said femoral base portion to provide a knee joint stabilizing trial device wherein said side walls are fixable in a position adjacent said groove and said cam has a portion extending from each of said side walls.

3. The modular femoral trial kit of claim 2 wherein said plurality of femoral base portions comprises at least two femoral bases having different sizes.

4. The modular femoral trial kit of claim 2 wherein said plurality of femoral base portions comprises a right femoral base and a left femoral base.

5. The modular femoral trial kit of claim 2 wherein said plurality of adapters comprises at least two stabilizing adapters wherein each of said adapters has a different stabilizing capacity.

* * * * *